United States Patent
Kim

(10) Patent No.: US 11,813,442 B2
(45) Date of Patent: Nov. 14, 2023

(54) INTRAVENOUS INJECTION AID FOR INDICATING VEIN

(71) Applicant: Jason Kim, Seoul (KR)

(72) Inventor: Jason Kim, Seoul (KR)

(*) Notice: Subject to any disclaimer, the term of this patent is extended or adjusted under 35 U.S.C. 154(b) by 0 days.

(21) Appl. No.: 17/811,139

(22) Filed: Jul. 7, 2022

(65) Prior Publication Data
US 2023/0181842 A1 Jun. 15, 2023

(30) Foreign Application Priority Data
Dec. 14, 2021 (KR) .......................... 10-2021-0178454

(51) Int. Cl.
*A61M 5/42* (2006.01)
*A61B 5/00* (2006.01)

(52) U.S. Cl.
CPC ............ *A61M 5/427* (2013.01); *A61M 5/425* (2013.01); *A61B 5/0064* (2013.01); *A61B 5/489* (2013.01); *A61M 2205/07* (2013.01); *A61M 2205/587* (2013.01); *A61M 2209/082* (2013.01); *A61M 2210/083* (2013.01)

(58) Field of Classification Search
CPC .. A61M 5/427; A61M 5/425; A61M 2205/07; A61M 2205/587; A61M 2209/082; A61M 2210/083; A61M 5/42; A61B 5/489; A61B 5/0064
See application file for complete search history.

(56) References Cited

U.S. PATENT DOCUMENTS

| 2011/0009751 A1* | 1/2011 | McGuire, Jr. ........ A61B 5/6833 600/473 |
| 2021/0212658 A1* | 7/2021 | McGrath ................ A61B 34/25 |

FOREIGN PATENT DOCUMENTS

| KR | 10-2013-0117763 B1 * | 3/2015 | ............. A61B 5/117 |
| KR | 10-1503838 B1 | 3/2015 | |
| KR | 10-2015-0036869 A | 4/2015 | |
| KR | 10-2018-0064941 A | 6/2018 | |
| KR | 10-2176196 B1 | 11/2020 | |

OTHER PUBLICATIONS

KR 20180064941 A, Inventor: Lee Myung Bok et al., Published Jun. 2018, machine translation included with original document (Year: 2018).*

* cited by examiner

*Primary Examiner* — Keith M Raymond
*Assistant Examiner* — Patrick M Mehl
(74) *Attorney, Agent, or Firm* — KORUS Patent, LLC; Seong Il Jeong

(57) ABSTRACT

The present invention relates to the intravenous injection aid for indicating vein, comprising: a compression strap; a binding means disposed at the opposite ends of the compression strap; a near-infrared lamp disposed at the compression strap; and a controller disposed on the compression strap for controlling the near-infrared lamp. The present invention as mentioned above may not only indicates vein with high visibility but also keep the vein from swaying or moving even during intravenous injection, so the intravenous injection can be carried out safely and efficiently.

4 Claims, 6 Drawing Sheets

INTRAVENOUS INJECTION AID FOR INDICATING VEIN

TECHNICAL FIELD

The present invention relates to an intravenous injection aid for indicating vein.

BACKGROUND ART

A visualization apparatus for vein has been disclosed in Korean Patent registration No. 1503838 (Registration date: Mar. 12, 2015. Title of the invention: Visualization apparatus for vein), which comprising: a near-infrared ray irradiating unit for irradiating near-infrared rays below the skin of target area; an infrared camera unit for photographing the target area; an image processing unit for receiving and processing image information of a portion below the skin of the target area taken by the infrared camera, and providing the processed image information to a display device; and a display device located near the target area and displaying image information provided by the image processing unit. The near-infrared ray irradiating unit has a predetermined inclination toward the target area direction so as to irradiate near-infrared rays to a portion below the skin of the target area through an outer skin of the target area. The near-infrared ray irradiating unit located inside of a barrier member, and the barrier member is used to prevent the infrared camera from capturing the near-infrared ray reflected from the outer skin surface of the target area.

According to the above previous technologies, since an operator may not only watch a near-infrared ray vein image through a display device but also directly see the skin of a target area, so that the venipuncture may be performed more accurately and intuitionally, and this technique may be applied to various operations which need visual checking of the veins in the skin. However, such technology can only display the position of the vein, it is not helpful for unskilled personnel in actual intravenous injections.

A real-time detection device of superficial vein has been disclosed in Korean Patent registration No. 2176196 (Registration date: Nov. 3, 2020. Title of the invention: Real-time detection device and method), which comprising: a near-infrared ray source module 100 for irradiate 800~950 nm band near-infrared ray to the skin; a camera module 200 comprises one or more lenses 210 for picking up the image of subcutaneous vessels and a near-infrared ray (IR) image sensor 220 for imaging images obtained from the lenses 210; an image processing module 300 for image processing the subcutaneous vessels data transmitted from the camera 200; and a digital light processing module (DLP) 400 that outputs the vessel images outputted from the image processing module 300 to the photographed skin area.

Before the vessel image is detected, the DLP module irradiates a datum point or datum line to the patient's skin, and the image processing module performs the image process for the image obtained from the camera module based on the datum point or datum line, then the DLP module outputs the images based on the datum point or datum line.

According to the above mentioned former technology, since the vessel images are projected to the in-situ accurately and real-timely, so can reduce the medical accident and the side effects in the IV infusion process; and when it is necessary to avoid vessels to perform the injection, the vessels will not be damaged, thus the burden of medical personnel can be reduced during IV infusion or plastic surgery, and patients may be actively diagnosed and treated, and the patients will also have an increased sense of trust in medical personnel because of the accurate operation, but on the other hand, although the visibility of vein is very high, since the vein moves during operation, it is difficult to operate accurately.

DISCLOSURE OF THE INVENTION

Technical Problem

To solve the above problem, an object of the present invention is to provide an intravenous injection aid for indicating vein, which can perform intravenous injection safely and efficiently.

Technical Solution

The object of the invention may be realized by the following intravenous injection aid for indicating vein. The intravenous injection aid comprises: a compression strap; a binding means disposed on opposite ends of the compression strap; a near-infrared lamp disposed at the compression strap; and a controller disposed at the compression strap for controlling the near-infrared lamp.

Preferably, the binding means is a hook-and-loop fastener or buckle type, the intravenous injection aid further comprising a lamp supporting component disposed at one surface of the compression strap, the near-infrared lamp is disposed at the lamp supporting component.

Preferably, the intravenous injection aid further comprises a first blood vessel fixing component disposed on the compression strap with a separating distance from the near-infrared lamp, the first blood vessel fixing component includes a first attaching component and a first release paper disposed on the lower surface of the first attaching component, the first blood vessel fixing component further includes a plurality of compression plates interposed between the lower surface of the first attaching component and the upper surface of the first release paper.

More preferably, the intravenous injection aid further comprises a second blood vessel fixing component disposed at one end of the first blood vessel fixing component, the second blood vessel fixing component includes a second attaching component, and a second release paper disposed at the lower surface of the second attaching component.

Preferably, the intravenous injection aid further comprises a compressing means disposed at the compression strap, the compressing means comprising a compression tube disposed in the compression strap, a connecting tube disposed at the compression strap and one end of the connecting tube connected with the compression tube, and an air supply apparatus connected with other end of the connecting tube.

Advantageous Effects

The present invention as mentioned above may not only indicate vein with high visibility but also keep the vein from swaying or moving even during intravenous injection, so the intravenous injection can be carried out safely and efficiently.

DETAILED DESCRIPTION

Hereinafter, embodiments of the present invention will be described with reference to the accompanying drawings.

Figure 1:
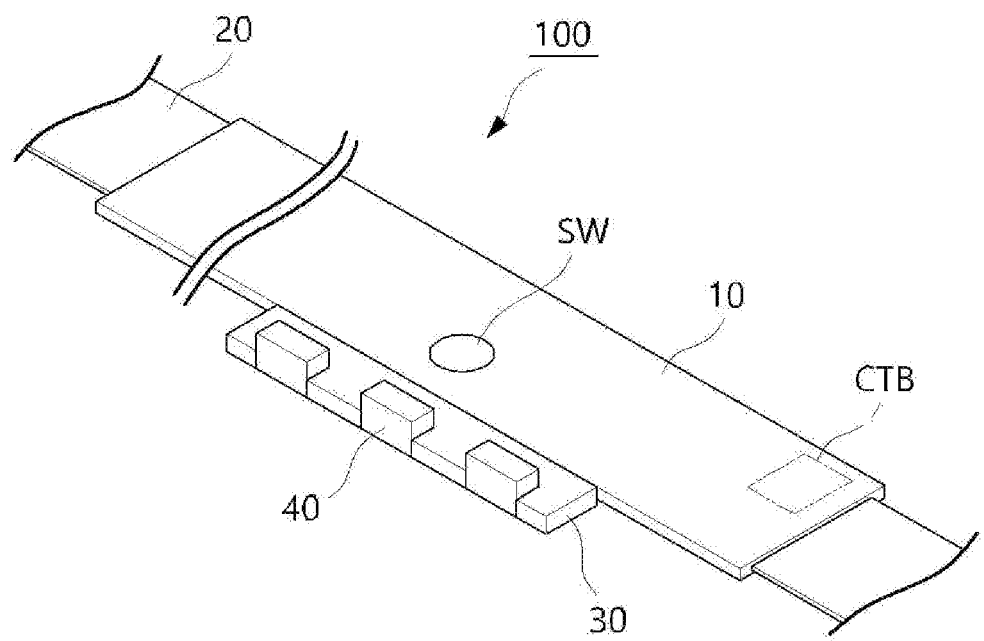
FIG. 1 is an oblique view of the intravenous injection aid for indicating vein according to an embodiment of the present invention.
Figure 2A:
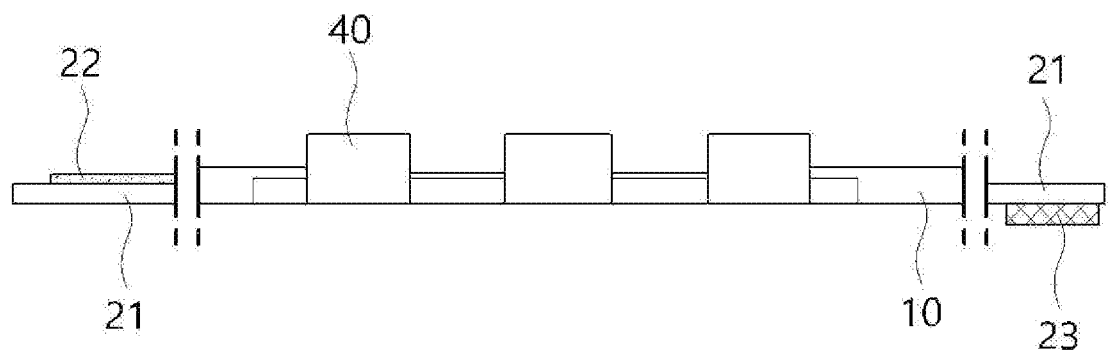
FIG. 2a is a side view of a hook-and-loop fastener type binding means of the intravenous injection aid for indicating vein shown in FIG. 1.
Figure 2B:
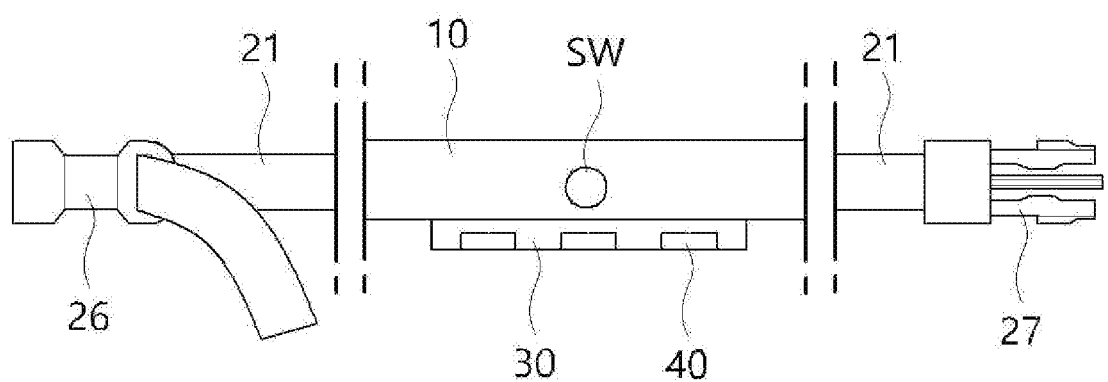
FIG. 2b is a vertical view of a buckle type binding means of the intravenous injection aid for indicating vein shown in FIG. 1.
Figure 3:
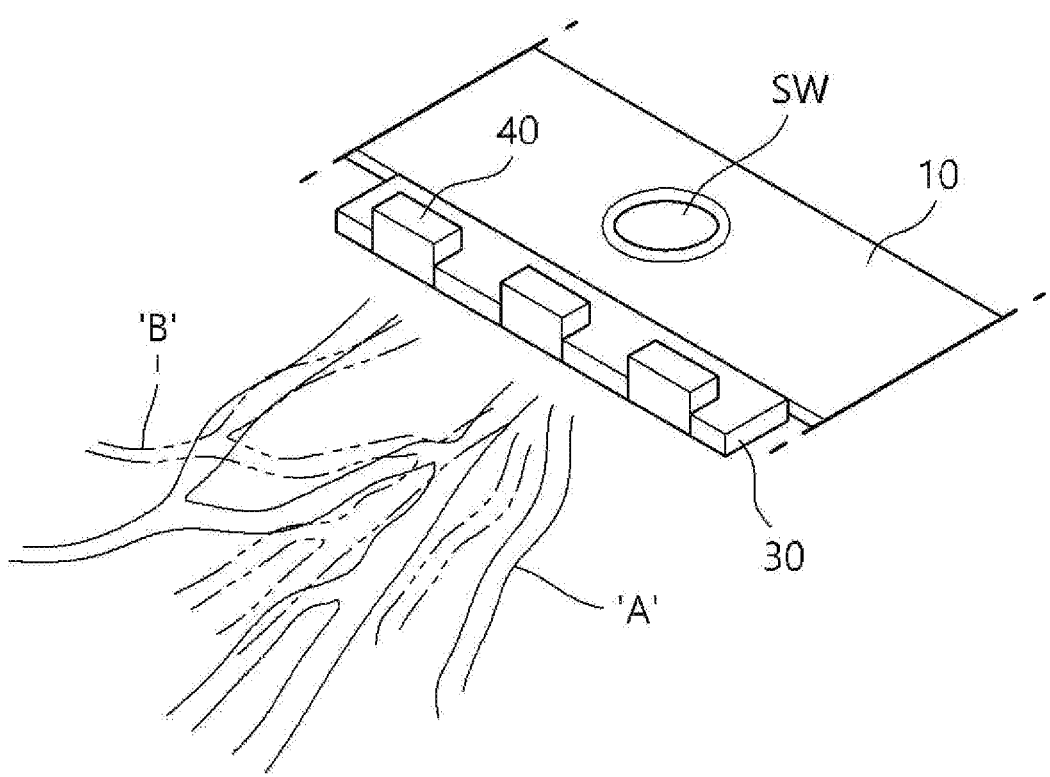
FIG. 3 is a partially enlarged oblique view of a using status of the intravenous injection aid for indicating vein shown in FIG. 1.

As shown in FIG. 1 to FIG. 3, the intravenous injection aid for indicating vein 100 according to the present invention may include a compression strap 10, a binding means 20, a lamp supporting component 30, a near-infrared lamp 40, and a controller (CTB).

The intravenous injection has the features that the pesticide effect can rapidly appear as the medicinal liquid reaches the required tissues of the body through the heart within 1-2 minutes. Therefore, the intravenous injection is used when water cannot be fully ingested orally to supply water, salinity, or other required electrolyte, or when need to inject antidote and other medications in the blood after bleeding, or expecting rapid pesticide effect. The intravenous drip is also a kind of the intravenous injection, because a large amount of liquid can be injected painlessly, which is used as an infusion means of liquid or blood transfusion.

The intravenous injection aid for indicating vein 100 according to this embodiment is provided to indicate vein with high visibility when an intravenous injection filled with a medicament, water, or blood is injected into a vein of a human body.

The compression strap 10 is made of synthetic fiber, rubber, or leather, and is close to human skin.

The binding means 20 is disposed on opposite ends of the compression strap 10.

The hook-and-loop fastener type binding means 20 shown in FIG. 2a includes a binding strap 21 disposed on opposite end of the compression strap 10, a hook fastener 22 provided on upper surface of one end of the binding strap 21, and a loop fastener 23 provided on the lower surface of other end of the binding strap 21.

The buckle type binding means 20 shown in FIG. 2b includes a binding strap 21 disposed at opposite ends of the compression strap 10, a male buckle component 27 provided at one end of the binding strap 21, and a female buckle component 26 provided at other end of the binding strap 21.

The binding means 20 of this embodiment is used to bulge the vein on the skin as the compression strap 10 pressurizes the wrist. This is only one of various embodiments, which can be performed through various deformations. Otherwise, such binding means 20 is only a well-known component, so the detailed description or illustration of it is omitted.

The lamp supporting component 30 is provided at the front surface of the compression strap 10.

The plurality of near-infrared lamps 40 are set apart from each other at the lamp supporting component 30. Herein, the near-infrared ray irradiated by the near-infrared lamp 40 has 800~950 nm band, which makes the subcutaneous vessels e.g., veins visible to the naked eye.

The controller (CTB) is disposed at the compression strap 10 to control the near-infrared lamps 40. Herein, the unspecified mark 'SW' is a switch arranged at compression strap 10 for switching the near-infrared lamps 40, which is controlled by the controller (CTB).

FIG. 3 shows a status that the wrist portion is pressurized by the compression strap 10 and the binding means 20, the pressurized vein is indicated with high visibility by near-infrared ray irradiated from the near-infrared lamp 40. Herein, 'A' denotes the veins with high visibility as the veins are irradiated near-infrared ray under a status that the veins are bulged on the skin by the compression strap 10, 'B' denotes the veins with reduced visibility as the movement of the vein during the intravenous injection.

The intravenous injection aid for indicating vein 100 according to an embodiment of the present invention makes the veins bulge by the compression strap 10 and the binding means 20, as a result, provides a better visibility of the veins, on the other hand, it causes the veins to move, so which cannot perform a safe and efficient infusion during the intravenous injection.

Figure 4:
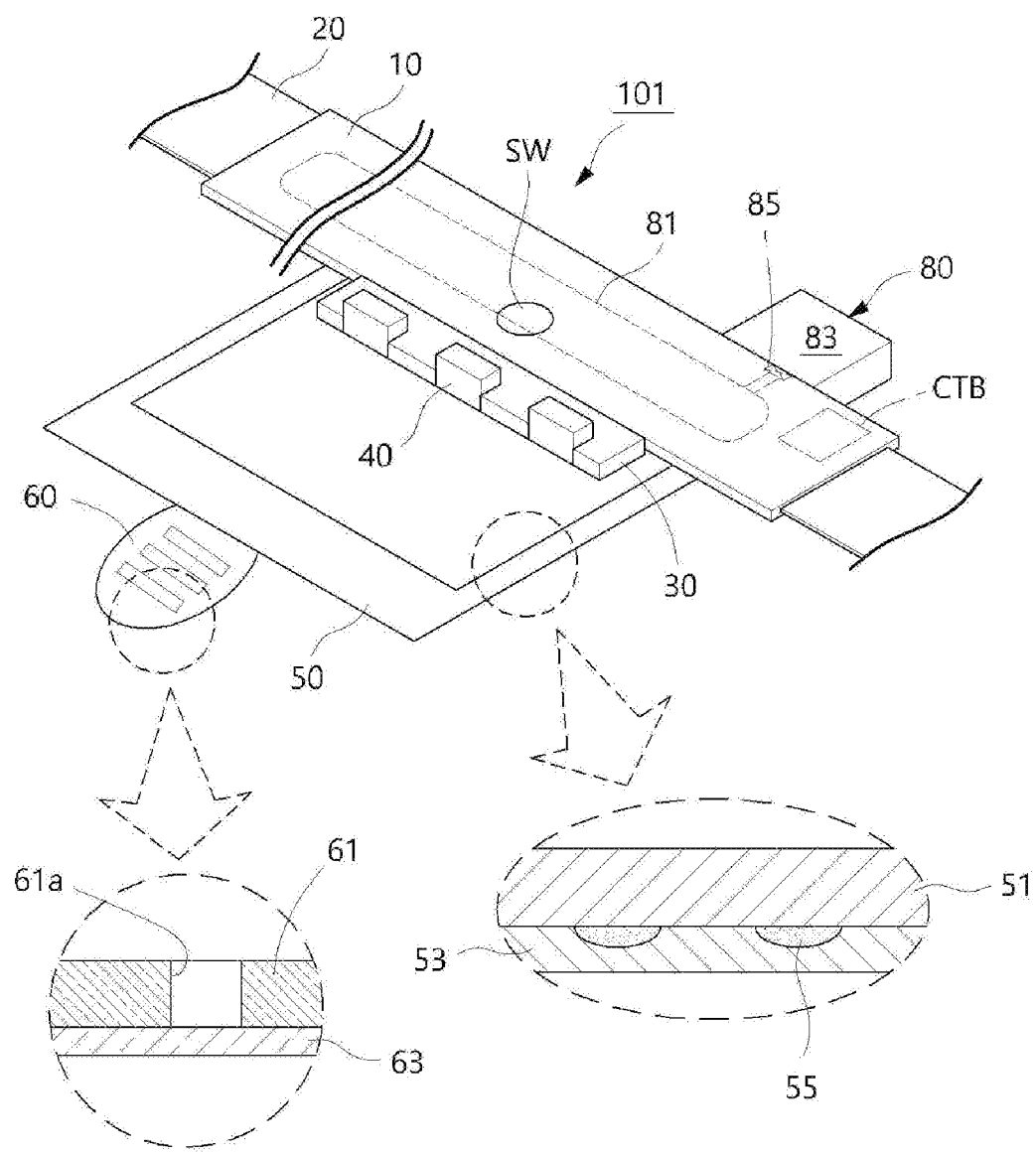
FIG. 4 is an oblique view of the intravenous injection aid for indicating vein according to an other embodiment of the present invention.
Figure 5:
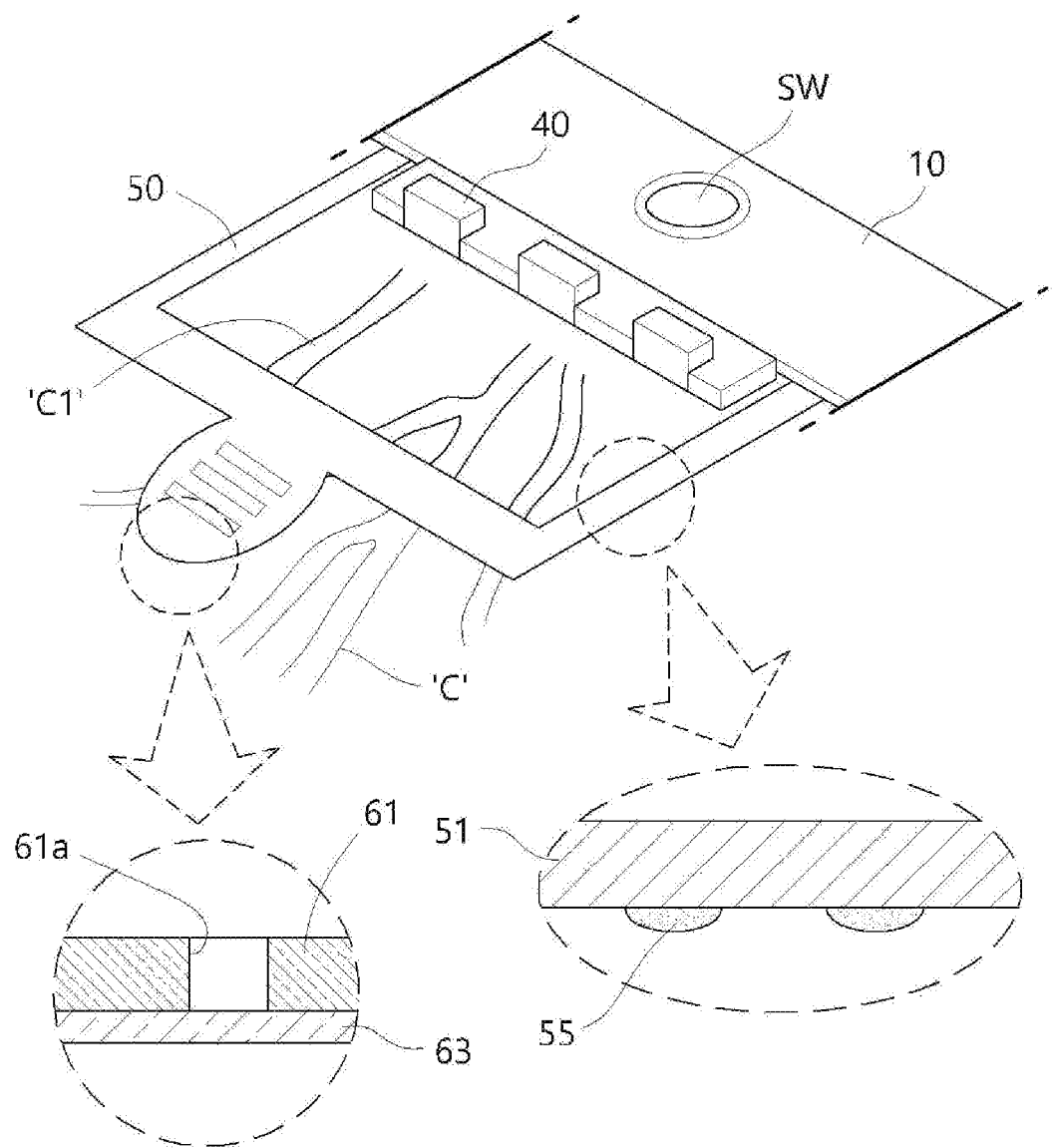
FIG. 5 and FIG. 6 are partially enlarged oblique views of a using status of the intravenous injection aid for indicating vein shown in FIG. 4.

As shown in FIG. 4, and FIG. 5, the intravenous injection aid for indicating vein 101 of other embodiment of the present invention may include a compression strap 10, a binding means 20, a lamp supporting component 30, a near-infrared lamp 40, a first blood vessel fixing component 50, a second blood vessel fixing component 60, a compressing means 80, and a controller (CTB).

The components of the other embodiment of the present invention i.e., a compression strap 10, a binding means 20, a lamp supporting component 30, a near-infrared lamp 40 and a controller (CTB) have the same structure with the one embodiment shown in FIG. 1 to FIG. 3, so the detailed description of it is omitted, and they are marked with the same reference symbols.

The first blood vessel fixing component 50 includes a first attaching component 51 provided at the front surface of the compression strap 10 with a separating distance from the near-infrared lamp 40, and a first release paper 53 provided at the lower surface of the first attaching component 51.

The first blood vessel fixing component 50 further includes a plurality of compression plates 55 that interposed between the lower surface of the first attaching component 51 and the upper surface of the first release paper 53.

The first blood vessel fixing component 50 is attached on the wrist skin, and which is provided to avoid the movement of the veins even during intravenous injection, the compression plate 55 is provided to press the skin to bulge the veins.

The first blood vessel fixing component 50 has a shape of 'U', but which is not limited such shape, which may be deformed into various shapes and is located and fixed in an irradiation direction of a near-infrared ray, so the veins cannot move and become more bulge.

The second blood vessel fixing component 60 includes a second attaching component 61 provided at one end of the first blood vessel fixing component 50, and a second release paper 63 provided at the lower surface of the second attaching component 61.

Figure 6:
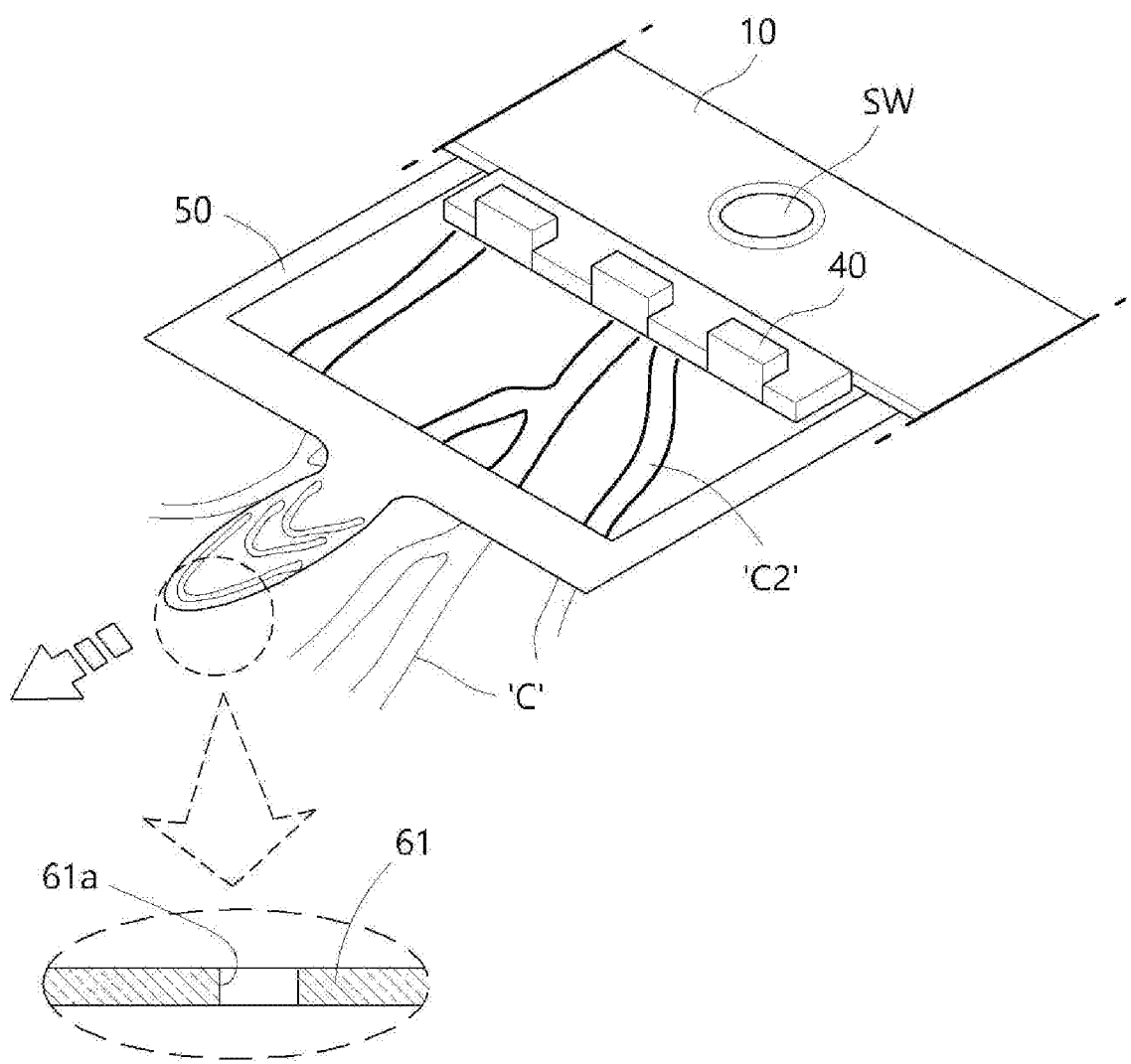

The second blood vessel fixing component 60 has a long groove 61a in width direction shown in FIG. 6, which is made to stretch easily. The second blood vessel fixing component 60 has the structure that after separating the second release paper 63, stretches the second release paper 63 in the arrow direction shown in FIG. 6, and then attaches it on the skin. Such structure has features that may easily achieve same or similar conditions as that during general intravenous injection, under the status of the medical personnel pressurizes the wrist, presses and pulls down the injection site to make the vein bulge and cannot move, then performs the intravenous injection.

The compressing means 80 comprises a compression tube 81 placed in the compression strap 10, a connecting tube 85 provided at the compression strap 10 and one end of the connecting tube 85 is connected to the compression tube 81, and an air supply apparatus 83 connected to other end of the connecting tube 85.

The air supply apparatus 83 is a hand air pump or an electric air pump, these elements are well-known components, so the detailed description or illustration of them will be omitted.

The FIG. 5 and FIG. 6 show the status that the wrist is pressed by the compression strap 10 and the binding means 20, and the vein is fixed and pressed by the first and second blood vessel fixing component 50, 60 so it cannot move. The pressed and fixed vein is indicated with high visibility by the near-infrared ray irradiated from the near-infrared lamp 40. Herein, 'C' denotes veins which located at the outside of the enclosed space formed by the compression strap 10 and the first blood vessel fixing component 50; 'C1' denotes veins which located in the enclosed space formed by the compression strap and the first blood vessel fixing component 50; 'C2' denotes veins which located in the enclosed space formed by the compression strap 10 and first blood vessel fixing component 50, and the second blood vessel fixing component 60 is attached on these veins. The practical intravenous injection will be infused in the 'C2' veins.

The operating relationship of the intravenous injection aid for indicating vein 101 with the above-mentioned structure will be briefly described below. The air supply apparatus 83 is an electric air pump.

The medical personnel wraps the compression strap 10 on the patient's wrist, and then binds it by the binding means 20. Then, the controller (CTB) is operated to drive the air supply apparatus 83 to supply air to the compression tube 81 to pressurize the wrist.

Then, the medical personnel removes the first release paper 53, and separates the first release paper 53 of the first blood vessel fixing component 50, then attaches the first attaching component 51 onto the skin of the wrist. And then, the medical personnel separates the second release paper 63 of the second blood vessel fixing component 60, after that stretches the second attaching component 61, and then attaches it onto the skin of the wrist.

Then, operate the switch (SW) to turn on the near-infrared lamps 40, and then the intravenous injection solution is injected into the vein C2 with visibility. The procedure after intravenous injection will be omitted.

Although the above present invention is described through one embodiment, but it is not limited to these embodiments. It will be apparent that all of the deformation examples according to the article spirit of the present invention belong to the scope of the present invention.

DESCRIPTION OF SYMBOLS

10: compression strap
20: binding means
30: lamp supporting component
40: near-infrared lamp
CTB: controller
100: intravenous injection aid for indicating vein

What is claimed is:

1. A intravenous injection aid for indicating vein, comprising:
    a compression strap;
    a binding means disposed on opposite ends of the compression strap;
    a near-infrared lamp disposed at the compression strap;
    a controller disposed at the compression strap for controlling the near-infrared lamp; and
    a first blood vessel fixing component disposed on the compression strap with a separating distance from the near-infrared lamp,
    wherein the first blood vessel fixing component includes a first attaching component, a first release paper disposed on a lower surface of the first attaching component, and a plurality of compression plates interposed between the lower surface of the first attaching component and an upper surface of the first release paper, and
    wherein the first blood vessel fixing component has a shape of 'U' and opposite ends of the first blood vessel fixing component are fixed to the compression strap such that an enclosed region is formed by the first blood vessel fixing component and the compression strap in an irradiation direction of the near-infrared lamp.

2. The intravenous injection aid for indicating vein of claim 1, further comprising a lamp supporting component disposed at one surface of the compression strap, wherein the binding means is a hook-and-loop fastener or buckle type, and the near-infrared lamp is disposed at the lamp supporting component.

3. The intravenous injection aid for indicating vein of claim 1, further comprising a second blood vessel fixing component disposed at one end of the first blood vessel fixing component, wherein the second blood vessel fixing component includes a second attaching component, and a second release paper disposed at the lower surface of the second attaching component.

4. The intravenous injection aid for indicating vein of claim 1, further comprising a compressing means disposed at the compression strap, wherein the compressing means includes a compression tube disposed in the compression strap, a connecting tube disposed at the compression strap and one end of the connecting tube connected with the compression tube, and an air supply apparatus connected with other end of the connecting tube.

* * * * *